United States Patent
Shimakura et al.

(10) Patent No.: US 11,058,894 B2
(45) Date of Patent: Jul. 13, 2021

(54) PARTICLE BEAM THERAPY DEVICE AND IRRADIATION FIELD FORMING METHOD

(71) Applicant: Hitachi, Ltd., Tokyo (JP)

(72) Inventors: Tomokazu Shimakura, Tokyo (JP); Chihiro Nakashima, Tokyo (JP); Satoshi Totake, Tokyo (JP); Kazuo Tomida, Tokyo (JP); Takeshi Fujita, Tokyo (JP)

(73) Assignee: HITACHI, LTD., Tokyo (JP)

( * ) Notice: Subject to any disclaimer, the term of this patent is extended or adjusted under 35 U.S.C. 154(b) by 0 days.

(21) Appl. No.: 16/675,517

(22) Filed: Nov. 6, 2019

(65) Prior Publication Data

US 2020/0261745 A1 Aug. 20, 2020

(30) Foreign Application Priority Data

Feb. 18, 2019 (JP) .............................. JP2019-026903

(51) Int. Cl.
*A61N 5/10* (2006.01)

(52) U.S. Cl.
CPC ........... *A61N 5/1043* (2013.01); *A61N 5/103* (2013.01); *A61N 2005/1087* (2013.01)

(58) Field of Classification Search
CPC ................ A61N 5/1043; A61N 5/1044; A61N 2005/1087
See application file for complete search history.

(56) References Cited

U.S. PATENT DOCUMENTS

| 2012/0132826 A1* | 5/2012 | Iwata | ..................... G21K 1/093 |
| | | | 250/396 ML |
| 2012/0199757 A1* | 8/2012 | Pu | ......................... G21K 1/093 |
| | | | 250/396 R |
| 2013/0140468 A1* | 6/2013 | Chen | ................... A61N 5/1043 |
| | | | 250/396 R |
| 2017/0216622 A1 | 8/2017 | Fujitaka et al. | |

FOREIGN PATENT DOCUMENTS

| JP | 08-257148 A | 10/1996 |
| JP | 2017-131399 A | 8/2017 |
| WO | 2012/008190 A1 | 1/2012 |

* cited by examiner

*Primary Examiner* — Eliza W Osenbaugh-Stewart
(74) *Attorney, Agent, or Firm* — Mattingly & Malur, PC

(57) ABSTRACT

To provide a particle beam therapy device that expands an irradiation field while avoiding an increase in size of a scanning unit or an irradiation device including the scanning unit. A shift unit 36 is provided downstream of a scanning unit 34. The shift unit 36 deflects a carbon beam as a particle beam to shift the irradiation field, thereby forming an expanded irradiation field. The shift unit 36 includes a first shift electromagnet 42 that shifts the irradiation field in a Y direction and a second shift electromagnet 44 that shifts the irradiation field in an X direction. The scanning unit is dynamically controlled, and the shift unit 36 is statically controlled.

10 Claims, 10 Drawing Sheets

PARTICLE BEAM THERAPY DEVICE AND IRRADIATION FIELD FORMING METHOD

CROSS-REFERENCE TO RELATED APPLICATION

The present application claims priority from Japanese application JP 2019-026903, filed on Feb. 18, 2019, the contents of which is hereby incorporated by reference into this application.

BACKGROUND OF THE INVENTION

1. Field of the Invention

The present invention relates to a particle beam therapy device and an irradiation field forming method, and particularly to a technique for expanding an irradiation field.

2. Description of the Related Art

A particle beam therapy device treats a target such as a malignant tumor by irradiating the target with a particle beam. Examples of particles constituting the particle beam include charged particles such as electrons, protons, helium ions, and carbon ions. A particle beam therapy device that utilizes carbon ions and heavier ions are commonly referred to as a heavy particle beam therapy device. With the heavy particle beam therapy device, a high therapeutic effect can be expected while reducing damage to normal tissues. Hereinafter, a carbon beam therapy device is taken as an example, and a configuration thereof will be described.

The carbon beam therapy device includes, for example, an ion source, a linear accelerator, a synchrotron, a transport device, and an irradiation device. Carbon ions generated by the ion source are accelerated in the linear accelerator, and the accelerated carbon ions are further accelerated in the synchrotron. In the synchrotron, energy of the carbon ions is increased up to the energy required for the irradiation. A cluster of carbon ions, which are extracted continuously or extracted as a pulse train from the synchrotron and have a certain level of energy, are introduced as a carbon beam to the irradiation device via the transport device. The target in the living body is irradiated with the carbon beam emitted from the irradiation device.

The irradiation device is provided with a scanning unit. The scanning unit performs scanning with the carbon beam in an X direction and a Y direction orthogonal to an irradiation center axis. The scanning unit generally includes an X-direction electromagnet for scanning and a Y-direction electromagnet for scanning. For example, as described in JP-A-2017-131399, a three-dimensional irradiation region that is irradiated with a carbon beam is divided into a plurality of layers in a traveling direction of the carbon beam, and a plurality of irradiation spots arranged on each layer are irradiated sequentially with a scanning carbon beam on a spot basis according to a predetermined order. In some cases, a rotating gantry is used such that a living body can be irradiated with the carbon beam from various angles within a range of ±180 degrees. The rotating gantry is a large structure which rotates and in which the irradiation device and part of the transport device are mounted.

In a particle beam therapy device described in WO2012/008190, two scanning units are used, which have different frequency response characteristics and are arranged side by side in an axial direction of a particle beam. The two scanning units operate in coordination, and are controlled dynamically and simultaneously. In a particle beam therapy device described in JP-A-8-257148, an electromagnet used for moving an irradiation field is provided upstream of an electromagnet for scanning. The electromagnet for scanning provided downstream of the electrode used for moving an irradiation field is mechanically moved accompanying the movement of the irradiation field, and an unrealistic aspect is recognized in the configuration.

In particle beam therapy, it is required to expand the irradiation field serving as a range in which irradiation with the particle beam can be performed for a purpose of treating a large target or other purposes. As a first method for expanding the irradiation field, there is a method of increasing a strength of a magnetic field for scanning. However, according to the first method, a size of the scanning unit may be increased, and a settling time of the magnetic field in the scanning unit may be increased. As a second method for expanding the irradiation field, there is a method of increasing a distance between the scanning unit and a target center point. However, according to the second method, a size of the irradiation device including the scanning unit may be increased.

SUMMARY OF THE INVENTION

An object of the invention is to form an irradiation field larger than an irradiation field formed only by a scanning unit in particle beam therapy. Alternatively, an object of the invention is to realize an irradiation field expanding method that is different from the first method and the second method in particle beam therapy.

A particle beam therapy device according to the invention includes: a scanning unit that performs scanning with a particle beam to form an irradiation field; and a shift unit that shifts the irradiation field by deflecting the particle beam emitted from the scanning unit to form an expanded irradiation field.

An irradiation field forming method according to the invention includes: a step of forming an irradiation field by performing scanning with a particle beam for treatment; and a step of forming an expanded irradiation field by shifting the irradiation field through deflecting the particle beam after the scanning.

According to the device and method of the invention, an irradiation field larger than an irradiation field formed only by a scanning unit can be formed.

DESCRIPTION OF THE PREFERRED EMBODIMENTS

Figure 1:
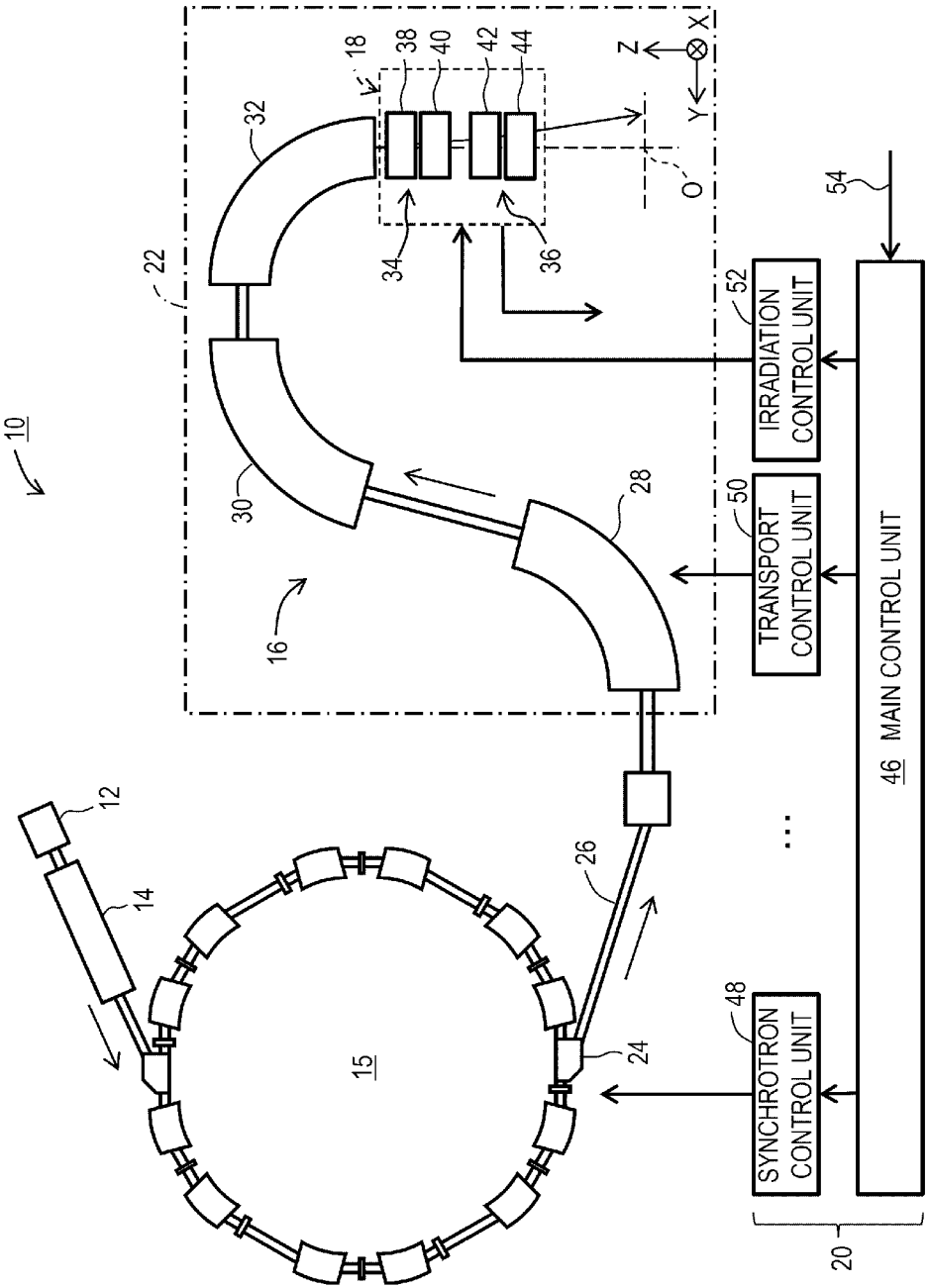
FIG. 1 is a schematic diagram illustrating a particle beam therapy device according to an embodiment.

Hereinafter, embodiments will be described with reference to the drawings.

(1) Overview of Embodiments

A particle beam therapy device according to an embodiment includes a scanning unit and a shift unit. The scanning unit is a mechanism that performs scanning with a particle beam to form an irradiation field. The shift unit is a mechanism that shifts the irradiation field by deflecting the particle beam emitted from the scanning unit to form an expanded irradiation field.

According to the configuration described above, the expanded irradiation field can be formed by the shift unit provided at a post-stage of the scanning unit. Therefore, when expanding the irradiation field, an increase in size of the scanning unit can be avoided, and there is no need to increase a distance from the scanning unit to a target center point. The irradiation field may be shifted after changing a configuration of the scanning unit or the distance from the scanning unit to the target center point. In other words, according to the configuration described above, as long as an expanded irradiation field of a required size can be obtained, the irradiation field formed only by a scanning unit can be reduced, so that an advantage of miniaturization of the scanning unit or miniaturization of the irradiation device including the scanning unit can be obtained.

The particle beam therapy device according to the embodiment includes a control unit that dynamically switches operation conditions of the scanning unit in a scanning period in which scanning with a particle beam is performed, and that statically switches operation conditions of the shift unit in an interruption period in which irradiation with the particle beam is not performed. A control device to be described below is one mode of the control unit.

The dynamic switching of the operation conditions of the scanning unit is performed to dynamically change an irradiation position. In the embodiment, the operation conditions of the scanning unit are repeatedly switched in an intermittent or continuous manner in the scanning period. The static switching of the operation conditions of the shift unit is in contrast with the dynamic switching described above, and means switching of the operation conditions performed in the interruption period for a single time in an irradiation field shift unit. In the embodiment, after an irradiation field shift, the operation conditions of the shift unit are maintained until the next irradiation field shift. If the irradiation field shift is performed in the interruption period in which the irradiation is stopped, unnecessary exposure in the living body can be prevented or reduced, that is, irradiation accuracy can be improved by performing irradiation in a beam dose according to a treatment plan.

For correction of a particle beam trajectory or other reasons, a modification is also considered in which the operation conditions of the shift unit are changed gently, that is, statically. Each operation condition includes, for example, a magnitude of a current which defines a strength of a magnetic field.

In the embodiment, the scanning unit includes a first scanning electromagnet that causes scanning with a particle beam in a first scanning direction orthogonal to a scanning central axial direction, and a second scanning electromagnet that causes scanning with the particle beam in a second scanning direction orthogonal to the scanning central axial direction and orthogonal to the first scanning direction, and the shift unit includes a first shift electromagnet that shifts the irradiation field in the first scanning direction.

The configuration described above expands the irradiation field at least in the first scanning direction. The first scanning direction is one direction of an X direction and a Y direction, which will be described later, and the second scanning direction is the other direction of the X direction and the Y direction, which will be described later.

In the embodiment, a settling time of a magnetic field formed by the first scanning electromagnet is shorter than a settling time of a magnetic field formed by the first shift electromagnet. In other words, inductance of the first scanning electromagnet is smaller than inductance of the first shift electromagnet. Generally, as the inductance increases, the settling time of the magnetic field increases.

As described above, in the configuration according to the embodiment, the scanning electromagnet in which a response characteristic is prioritized and the shift electromagnet in which a deflection characteristic is prioritized are used in combination to achieve both miniaturization of the irradiation device and the expansion of the irradiation field. In particular, since the statically controlled shift unit is provided at the post-stage of the dynamically controlled scanning unit, various challenges in designing, manufacturing, and controlling the irradiation device are greatly reduced.

In the embodiment, the number of shift stages in the first scanning direction in the shift unit is m (where m is an odd number of 3 or more). In the embodiment, by changing a direction of the current, a shift direction (positive direction or negative direction) is switched, and the presence or absence of shift is switched by ON/OFF of the current. That is, the irradiation field shift can be realized by simple control.

In the embodiment, the shift unit includes a second shift electromagnet that shifts the irradiation field in the second scanning direction. According to this configuration, it is possible to move the irradiation field in the first scanning direction and the second scanning direction by using the first shift electromagnet and the second shift electromagnet. A shift amount in each scanning direction can be varied stepwise or continuously. In a case of being varied continuously, the shift direction and shift amount of the irradiation field can be arbitrarily determined.

In the embodiment, the number of shift stages in the first scanning direction in the shift unit is m (where m is an odd number of 3 or more), and the number of shift stages in the second scanning direction in the shift unit is n (where n is an odd number of 3 or more), and the expanded irradiation field is equivalent to a set of m×n irradiation field divisions. When the number of shift stages is included in a case of no shift in the case of the current OFF, each of m and n is generally an odd number. The irradiation field division is one unit constituting the expanded irradiation field, and an entity thereof is an irradiation field.

In the embodiment, whether to shift the irradiation field is determined according to energy of the particle beam. When the particle beam passes through the magnetic field, a bending degree of the trajectory of the particle beam changes depending on the energy of the particle beam (precisely, the particle). When the energy of the particle beam is low, an irradiation field having a size equal to that of the scanning unit can be formed. But when the energy of the particle beam is high, it is difficult to form a large irradiation field. Therefore, the configuration described above switches the presence or absence of the irradiation field shift according to the energy of the particle beam. Whether to shift the irradiation field may be determined during treatment, or may be determined in a treatment planning stage. In either case, a part that makes such a determination can be regarded as a part of the control unit.

The particle beam therapy device according to the embodiment includes a reference image forming unit that forms a reference image including a tissue image. The reference image includes a division image that is an image synthesized on the tissue image and that represents a plurality of irradiation field divisions formed by the irradiation field shift. The reference image is displayed in at least one of the treatment planning stage and the treatment stage.

According to the configuration described above, it is possible to make a treatment plan based on the irradiation field shift during the treatment, or it is possible to observe the tissue image, in comparison with a plurality of irradiation field divisions set by the irradiation field shift during the treatment.

An irradiation field forming method according to the embodiment includes: a step of generating an irradiation field by performing scanning with a particle beam for treatment; and a step of generating an expanded irradiation field by shifting the irradiation field through deflecting the particle beam after the scanning.

(2) Detailed Description of Embodiments

FIG. 1 is a schematic diagram illustrating an overall configuration of the particle beam therapy device according to the embodiment. Specifically, the illustrated particle beam therapy device is a carbon beam therapy device 10. The carbon beam therapy device 10 is a medical device that performs treatment by irradiating a target in a living body with a carbon beam. In the carbon beam therapy device 10, an irradiation field forming method to be described below is performed. The configuration to be described below may also be applied to other particle beam therapy devices such as a proton beam therapy device.

In the illustrated configuration example, the carbon beam therapy device 10 includes an ion source 12, a linear accelerator 14, a synchrotron 15 as a circular accelerator, a transport device 16, an irradiation device 18, a control device 20, and the like. A portion of the transport device 16, and the irradiation device 18 are attached to a housing of a rotating gantry 22. The rotating gantry 22 is a rotating structure for irradiating the living body with a carbon beam from an arbitrary direction within a range of ±180 degrees. The following configurations may be applied to a particle beam therapy device that includes a half gantry, as an alternative to the rotating gantry, capable of performing irradiation with a carbon beam from an arbitrary direction within a range of 270 degrees or less, or may be applied to a particle beam therapy device without a rotating gantry.

In the ion source 12, carbon ions are generated. The linear accelerator 14 preliminarily accelerates the carbon ions. The ion source 12 and the linear accelerator 14 are also referred to as an injection system. An injection system other than the illustrated may be adopted.

The synchrotron 15 functions as a main accelerator. Specifically, the synchrotron 15 accelerates the carbon ions to increase the energy thereof. A depth at which the carbon ions reach in the living body depends on the energy of the carbon ions. In the synchrotron 15, the energy of the carbon ions is increased to a level corresponding to an irradiation point depth (layer depth). The energy can be varied by varying a frequency that defines a circulation time. Instead of the synchrotron 15, other accelerators such as a cyclotron or a synchrocyclotron may be used. From a beam extractor 24 in the synchrotron 15, a cluster of carbon ions having a certain level of energy are extracted as a carbon beam. In this case, whether the carbon beam is continuously extracted or is extracted as a pulse train depends on an irradiation method. The irradiation and non-irradiation with the carbon beam are switched by controlling an operation of the synchrotron 15.

The carbon beam is sent to the irradiation device 18 via the transport device 16 including a transport tube 26 and the like. In the illustrated configuration example, the transport device 16 includes three deflection electromagnets 28, 30 and 32. A trajectory of the carbon beam is bent by each of the deflection electromagnets 28, 30 and 32. The transport device 16 includes a plurality of quadrupole electromagnets that focus or shape the carbon beam, but illustration thereof is omitted. The individual electromagnets are connected to power sources, but illustration thereof is also omitted.

In the illustrated configuration example, the irradiation device 18 is provided at a post-stage, that is, downstream of the deflection electromagnet 32 at a final stage in the traveling direction of the carbon beam emitted from the synchrotron 15. FIG. 1 illustrates the irradiation device 18 according to a first example. The irradiation device 18 includes a scanning unit 34 and a shift unit 36. Specifically, the shift unit 36 is provided downstream of the scanning unit 34.

In FIG. 1, a Z direction is a direction parallel to the traveling direction (specifically, the scanning central axial direction) of the carbon beam. The Y direction orthogonal to the Z direction is a direction parallel to a rotation center axis of the gantry. The X direction is a direction orthogonal to the Z direction and the Y direction. An isocenter O is the target center point, which is defined as an intersection point of the scanning center axis and the rotation center axis of the rotating gantry 22.

The scanning unit 34 is a mechanism that performs a two-dimensional scanning with the carbon beam. That is, the scanning unit 34 performs scanning with the carbon beam in the Y direction and the X direction. An irradiation field as a two-dimensional scanning region is formed by the two-dimensional scanning with the carbon beam. Generally, the irradiation field can be defined as a two-dimensional scanning region on a plane that is orthogonal to the scanning center axis and that crosses the isocenter O.

Specifically, the scanning unit 34 includes a first scanning electromagnet 38 and a second scanning electromagnet 40 that are arranged in order from an upstream side in the traveling direction of the carbon beam. For example, the first scanning electromagnet 38 is an electromagnet that deflects the carbon beam in the Y direction with the action of a magnetic field for scanning, and the second scanning electromagnet 40 is an electromagnet that deflects the carbon beam in the X direction with the action of a magnetic field for scanning. In the embodiment, the first scanning electromagnet 38 can perform scanning at a higher speed than the second scanning electromagnet 40. Performance of the first scanning electromagnet 38 and performance of the second scanning electromagnet 40 may be the same. Scanning directions and scanning speeds may be exchanged between the first scanning electromagnet 38 and the second scanning electromagnet 40.

The shift unit 36 is a mechanism that shifts the irradiation field formed by the scanning unit 34 by bending the trajectory of the particle beam with the magnetic field. In other words, the shift unit 36 is a mechanism that forms a large irradiation field that cannot be obtained only by the scanning unit 34. Specifically, in the first example, the shift unit 36 includes a first shift electromagnet 42 and a second shift electromagnet 44 that are arranged in order from the upstream side in the traveling direction of the carbon beam. For example, the first shift electromagnet 42 is an electromagnet that further deflects the carbon beam, which is deflected by the scanning unit 34, with the action of a magnetic field thereof to shift the irradiation field toward the Y direction. The second shift electromagnet 44 is an electromagnet that further deflects the carbon beam, which is deflected by the scanning unit 34, with the action of a magnetic field thereof to shift the irradiation field toward the X direction. Scanning directions of the first shift electromagnet 42 and the second shift electromagnet 44 may be exchanged. A large irradiation field obtained by the shift unit 36 shifting the irradiation field formed by the scanning unit 34 is referred to as an expanded irradiation field.

By switching ON/OFF of a current supply to the first shift electromagnet 42 and switching of directions of the current supplied to the first shift electromagnet 42, a +Y direction shift, a −Y direction shift, or no shift is selected. In this case, the number of shift stages (m) is 3. Similarly, by switching ON/OFF of a current supply to the second shift electromagnet 44 and switching of directions of the current supplied to the second shift electromagnet 44, a +X direction shift, a −X direction shift, or no shift is selected with respect to the X direction. In this case, the number of shift stages (n) is 3.

In the first example, nine shift modes including a case of no shift can be realized by the shift unit 36. Accordingly, an expanded irradiation field nine times the magnitude of the irradiation field formed by the scanning unit 34 can be formed. Therefore, a large target that can enter the expanded irradiation field can be irradiated with the carbon beam without changing a position of a patient.

The first scanning electromagnet 38 and the first shift electromagnet 42 have the same function in deflecting the carbon beam toward the Y direction, but the first scanning electromagnet 38 is an electromagnet that operates at a high speed, in other words, an electromagnet that is dynamically controlled. In contrast, the first shift electromagnet 42 is an electromagnet that operates at a low speed, in other words, an electromagnet that is statically controlled.

In quantitative comparison, a settling time of the magnetic field of the first scanning electromagnet 38 is shorter than a settling time of the magnetic field of the first shift electromagnet 42. The settling time of the magnetic field of the first scanning electromagnet 38 is, for example, about several tens of microseconds, and the settling time of the magnetic field of the first shift electromagnet 42 is, for example, about several milliseconds. Generally, the settling time of the magnetic field is a time period from setting or changing of a generation condition of the magnetic field until fluctuation of the magnetic field falls within a certain range determined by using a target value as a reference.

From another viewpoint, inductance of the first scanning electromagnet 38 is smaller than inductance of the first shift electromagnet 42. The number of coil turns of the first scanning electromagnet 38 is considerably small, for example, about 10 turns. By applying a large current to the first scanning electromagnet 38, a scanning magnetic field having a strength required for the scanning with the carbon beam is formed. The number of coil turns of the first shift electromagnet 42 is relatively large, for example, about 100 turns. By applying a relatively small current to the first shift electromagnet 42, a shift magnetic field having a strength required to bend the carbon beam is formed. Any numerical value described in the specification is merely an example.

A relationship between the second scanning electromagnet 40 and the second shift electromagnet 44 is similar to a relationship between the first scanning electromagnet 38 and the first shift electromagnet 42. That is, the second scanning electromagnet 40 and the second shift electromagnet 44 have the same function of deflecting the carbon beam toward the X direction, but the second scanning electromagnet 40 is an electromagnet that operates at a high speed, in other words, an electromagnet that is dynamically controlled. In contrast, the second shift electromagnet 44 is an electromagnet that operates at a low speed, in other words, an electromagnet that is statically controlled. A settling time of the magnetic field of the second scanning electromagnet 40 is shorter than a settling time of the magnetic field of the second shift electromagnet 44. Inductance of the second scanning electromagnet 40 is smaller than inductance of the second shift electromagnet 44. Correction is applied in a case where an irradiation field size or magnification is changed by the irradiation field shift.

In the irradiation device 18, a beam dose monitor, a carbon beam position monitor, a ridge filter, and the like are provided downstream of the shift unit 36, but illustration thereof is omitted in FIG. 1. Similarly, in FIG. 1, illustration of a treatment table on which a living body is placed, an X-ray irradiation device, an X-ray detection device, and the like is omitted.

The first scanning electromagnet 38 and the second scanning electromagnet 40 may be integrated, and the first shift electromagnet 42 and the second shift electromagnet 44 may be integrated. The scanning unit 34 and the shift unit 36 are separated from each other in FIG. 1, and alternatively the shift unit 36 may be brought close to the scanning unit 34.

The control device 20 typically includes a plurality of information processing devices. Each information processing device includes a CPU that operates according to a program. In the illustrated configuration example, the control device 20 includes a main control unit 46 and a plurality of individual control units. The main control unit 46 controls the entire carbon beam therapy device 10 via the plurality of individual control units. The main control unit 46 is provided with treatment plan information 54 from a treatment planning device. The treatment planning device may be provided in the main control unit 46. A reference image forming unit to be described below may be provided in the main control unit 46.

The plurality of individual control units includes a synchrotron control unit 48, a transport control unit 50, and an irradiation control unit 52. Illustration of other individual control units is not omitted. The synchrotron control unit 48 controls the energy of the carbon beam by frequency control. The synchrotron control unit 48 also controls irradiation and non-irradiation with the carbon beam. The irradiation control unit 52 controls the scanning unit 34 and the shift unit 36. When controlling the shift unit 36, the irradiation control unit 52 controls switching of ON/OFF of the current supply to the first shift electromagnet 42, switching of the direction of the current supplied to the first shift electromagnet 42, switching of ON/OFF of the current supply to the second shift electromagnet 44, and switching of the direction of the current supplied to the second shift electromagnet 44. Accordingly, the irradiation field is shifted stepwise, and the expanded irradiation field is formed.

However, since the irradiation field having a large size can be formed by the scanning unit 34 when the energy of the carbon beam is low, there is a low necessity of the irradiation field shift. The irradiation control unit 52 performs the irradiation field shift when a value of the energy of the carbon beam is equal to or greater than a predetermined value. When the target is within the irradiation field in a non-shifted state, the irradiation field shift is not necessary.

Figure 2:
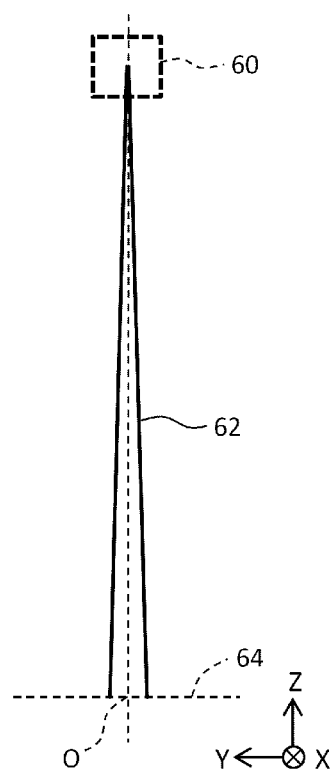
FIG. 2 is a diagram illustrating formation of an irradiation field according to a comparative example.
Figure 3:
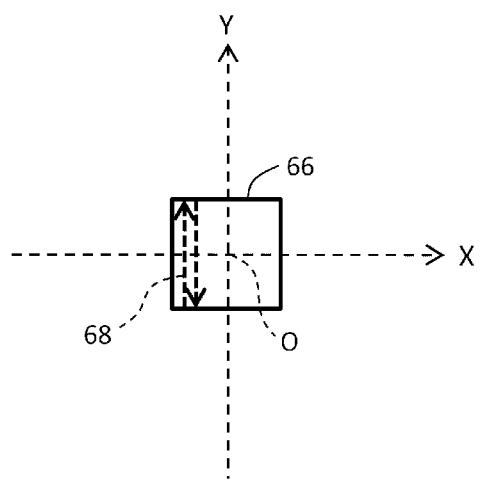
FIG. 3 is a diagram illustrating the irradiation field according to the comparative example.

FIGS. 2 and 3 illustrate comparative examples. FIG. 2 illustrates a scanning magnetic field 60 formed by the scanning unit. The scanning magnetic field 60 is a Y-direction scanning magnetic field, and illustration of an X-direction scanning magnetic field is omitted. By performing carbon beam scanning 62 in the Y direction, and by performing carbon beam scanning in the X direction, which is not illustrated in FIG. 2, an irradiation field is defined on an irradiation plane 64. The irradiation plane 64 is a virtual surface that passes through the isocenter O and that is orthogonal to the scanning center axis.

FIG. 3 illustrates an irradiation field 66 according to the comparative example. In FIG. 3, a horizontal axis corresponds to the X direction, and a vertical axis corresponds to the Y direction. Reference numeral 68 indicates Y direction scanning of an irradiation point. In the illustrated example, the Y direction is a high-speed scanning direction (main scanning direction), and the X direction is a low-speed scanning direction (sub-scanning direction). As illustrated in the comparative example, in order to expand the irradiation field by the scanning unit, it is necessary to increase the strength of the magnetic field for increasing a deflection angle of the carbon beam in the scanning unit, or to increase the distance between the scanning unit and the isocenter O. However, according to the former method, it is necessary to increase a distance between magnetic poles to allow the greatly deflected carbon beam to pass, or to increase the number of coil turns to increase the magnetic field strength, which leads to an increase in the size of the scanning unit. In addition, the inductance thereof is increased due to increase in the number of coil turns, resulting in an increase in the settling time of the magnetic field, that is, a decrease in the scanning speed. Meanwhile, according to the latter method, in order to secure the distance between the scanning unit and the isocenter O, the irradiation device and the rotating gantry including the irradiation device are increased in size. The increase in size of the irradiation device and the rotating gantry also leads to an increase in manufacturing cost and deterioration in irradiation position accuracy of the carbon beam.

Figure 4:
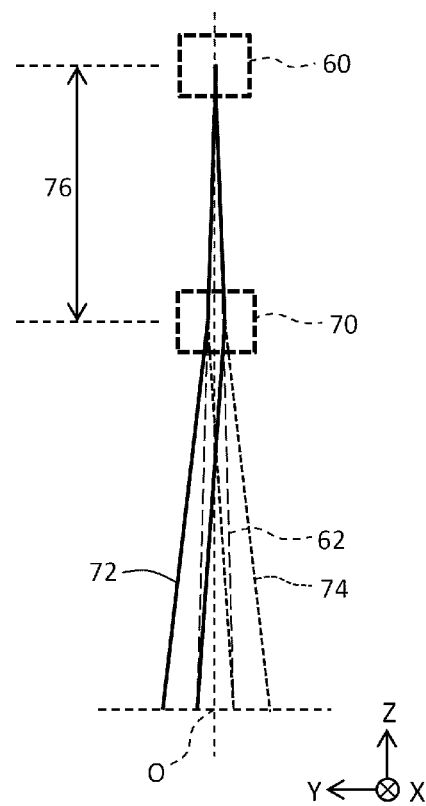
FIG. 4 is a diagram illustrating formation of an expanded irradiation field according to a first example.
Figure 5:
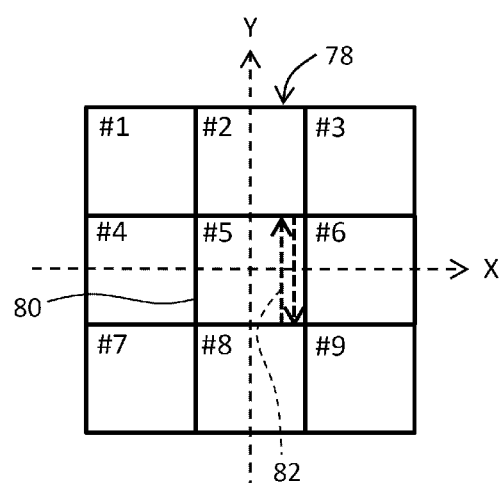
FIG. 5 is a diagram illustrating the expanded irradiation field according to the first example.

FIGS. 4 and 5 illustrate the first example. In FIG. 4, the scanning magnetic field formed by the scanning unit is indicated by reference numeral 60, and a shift magnetic field formed by the shift unit is indicated by reference numeral 70. The scanning magnetic field 60 is a Y-direction scanning magnetic field, and the shift magnetic field 70 is a Y-direction shift magnetic field. Illustration of the X-direction scanning magnetic field and an X-direction shift magnetic field are omitted.

Reference numeral 62 indicates a scanning range of the carbon beam in a case of no shift in the Y direction, reference numeral 72 indicates a scanning range of the carbon beam in a case where a shift toward the +Y direction is performed, and reference numeral 74 indicates a scanning range of the carbon beam in a case where a shift toward a −Y direction is performed. Similar switching control is also applied in the X direction.

As a result, as illustrated in FIG. 5, an expanded irradiation field 78 having a size nine times that of an original irradiation field 80 can be formed. The expanded irradiation field 78 is a set of nine irradiation field divisions #1 to #9. Each of the irradiation field divisions #1 to #9 is one unit constituting the expanded irradiation field 78, and the entity thereof is an irradiation field. Reference numeral 82 indicates Y direction scanning of an irradiation point in one irradiation field division.

Figures 6, 7:
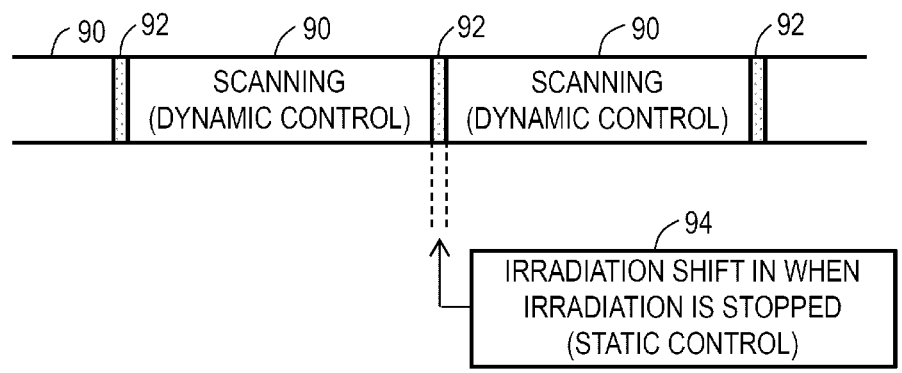
FIG. 6 is a diagram illustrating operations of a shift unit in the first example.
FIG. 7 is a diagram illustrating an example of an irradiation sequence.

FIG. 6 illustrates a control method of the shift unit in the first example. Reference numeral 84 indicates a control condition of the first shift electromagnet that performs the shift toward the Y direction. As described above, when the current is not applied to the first shift electromagnet (a case of OFF), the shift toward the Y direction is not performed. When the direction of the current applied to the first shift electromagnet is made to be a positive direction (a case of +), a magnetic field that causes the carbon beam to bend toward the +Y direction is generated. When the direction of the current applied to the first shift electromagnet is made to be a negative direction (a case of −), a magnetic field that causes the carbon beam to bend toward the −Y direction is generated.

Reference numeral 86 indicates a control condition of the second shift electromagnet that performs the shift toward the X direction. As described above, when the current is not applied to the second shift electromagnet (a case of OFF), the shift toward the X direction is not performed. When the direction of the current applied to the second shift electromagnet is made to be a positive direction (a case of +), a magnetic field that causes the carbon beam to bend toward the +X direction is generated. When the direction of the current applied to the second shift electromagnet is made to be a negative direction (a case of −), a magnetic field that causes the carbon beam to bend toward the −X direction is generated. The nine irradiation field divisions #1 to #9 are formed as described above by three shift stages in the Y direction and three shift stages in the X direction. A desired irradiation field division is selected from the nine irradiation field divisions #1 to #9 with a simple method of current control.

As described above, according to the first example, in comparison with the comparative example, it is possible to form an expanded irradiation field that is expanded three times in the X direction and the Y direction while maintaining the configuration of the scanning unit. Since the shift unit is statically controlled, it is relatively easy to manufacture the shift unit.

FIG. 7 illustrates an irradiation sequence. Although the illustrated irradiation sequence is executed in the first example, the same irradiation sequence may be applied to other examples to be described below. In each scanning period 90, scanning (irradiation) with the carbon beam is performed in a selected irradiation field division. At this time, dynamic control is applied to the scanning unit. That is, the scanning unit is controlled such that the irradiation position is continuously or intermittently changed.

An interruption period 92 is provided between two adjacent scanning periods 90. In each interruption period 92, irradiation with the carbon beam is stopped in order to prevent unnecessary exposure in the living body. As indicated by reference numeral 94, in such a state where the irradiation is stopped, the operation conditions of the shift unit are switched, and the irradiation field is shifted. That is, a change from a current irradiation field division to a next irradiation field division is performed. The above irradiation field shift can be referred to as static control in contrast with the dynamic control described above. After setting of the operation conditions for the shift unit is completed and the magnetic field is settled, the irradiation with the carbon beam is restarted. In each scanning period, the operation condition of the shift unit is maintained. However, the operation conditions may be changed statically or gently according to the necessity of magnetic field correction or the like. Each scanning period 90 is, for example, in a range of several hundreds of milliseconds to several seconds, and each interruption period 92 is, for example, several milliseconds.

Figure 8:
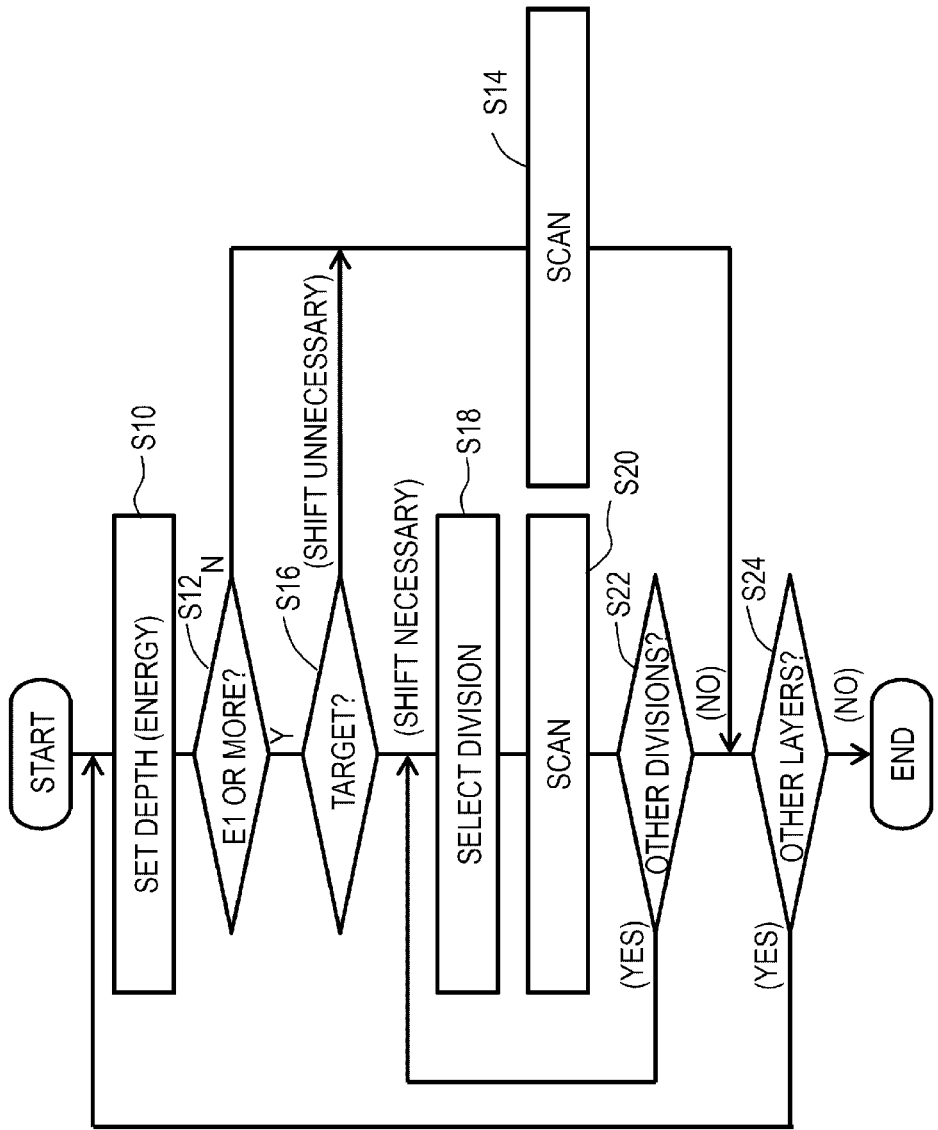
FIG. 8 is a flowchart illustrating operations of the particle beam therapy device according to the embodiment.

FIG. 8 illustrates operations in the first example by using a flowchart. Each step illustrated in FIG. 8 is also performed in other examples described below.

In S10, a depth is set by control from the main control unit. Accordingly, energy E of the carbon beam is set. Since a certain large irradiation field can be formed when the energy E is less than a threshold value E1, it is determined that a shift operation is not necessary, and S14 is performed. In S14, scanning with the carbon beam is performed by the scanning unit 34.

Meanwhile, when it is determined in S12 that the energy E is equal to or greater than the threshold value E1, it is determined in S16 whether the irradiation field shift is necessary, that is, whether an expanded irradiation field is required to be formed, in consideration of a size of the target that is an irradiation target. When it is determined that the irradiation field shift is not necessary, S14 described above is performed. When it is determined that the irradiation field shift is necessary, S18 is performed. In S18, an irradiation field division is selected. That is, a shift mode is selected. After the setting of the shift unit is completed, the scanning with the carbon beam is performed in the selected irradiation field division. Thereafter, when it is determined in S22 that irradiation for another irradiation field division is necessary, a new irradiation field division is selected in S18, and then the scanning with the carbon beam with respect to the irradiation field division is performed in S20. This process is repeated until the entire target in a currently selected layer is irradiated with the carbon beam.

In S24, it is determined whether a change to another layer is necessary. When it is determined that the change is necessary, the process returns to S10. In S10, the energy of the carbon beam corresponding to a depth of a next layer is set. Thereafter, the step of S12 and subsequent steps are repeatedly performed.

Note that S10 may be performed in the treatment planning stage. In such a case, actual irradiation control is performed according to a result of determining whether the shift is necessary according to the energy of the carbon beam.

Figure 9:
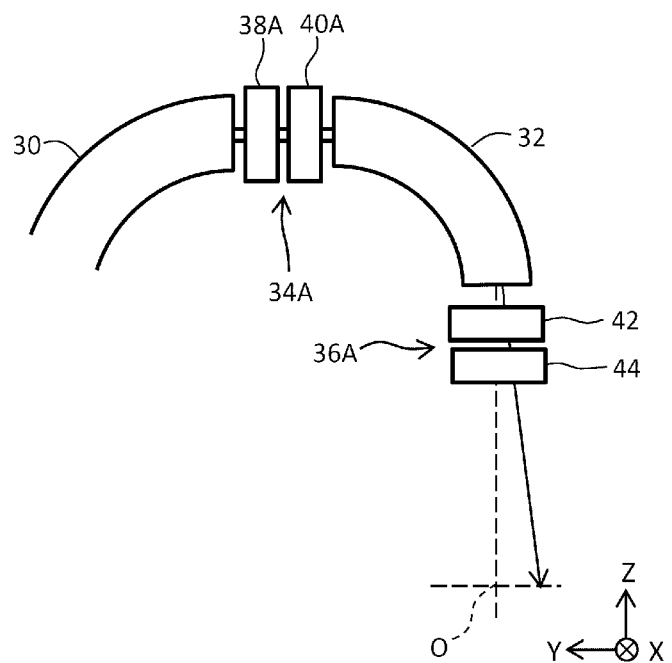
FIG. 9 is a schematic diagram illustrating a second example.

FIG. 9 illustrates an irradiation device according to a second example. The same elements as those illustrated in FIG. 1 are denoted by the same reference numerals, and a description thereof will be omitted. This also applies to the figures subsequent to FIG. 10.

In the second example as illustrated in FIG. 9, a scanning unit 34A is provided between the deflection electromagnet 30 and the deflection electromagnet 32. The scanning unit 34A includes a first scanning electromagnet 38A and a second scanning electromagnet 40A. The first scanning electromagnet 38A is equivalent to the first scanning electromagnet 38 illustrated in FIG. 1, and the second scanning electromagnet 40A is equivalent to the second scanning electromagnet 40 illustrated in FIG. 1.

A shift unit 36A is provided downstream of the deflection electromagnet 32 without the scanning unit positioned therebetween. Similarly to the first example, the shift unit 36A includes the first shift electromagnet 42 and the second shift electromagnet 44. With such a configuration, it is also possible to form an expanded irradiation field through irradiation field shift by the scanning unit.

When a large irradiation field is to be formed only by the scanning unit 34A without providing the shift unit 36A, it is necessary to increase a maximum scanning angle in the scanning unit 34A, and accordingly, it is necessary to use a deflection electromagnet having a large gap width as the deflection electromagnet 32. In contrast, according to the second example, since a scanning angle in the scanning unit 34A can be reduced, a deflection electromagnet having a small gap width can be used as the deflection electromagnet 32. In this case as well, a large irradiation field can be formed. The gap width is a size or distance between a pair of magnetic poles.

Figure 10:
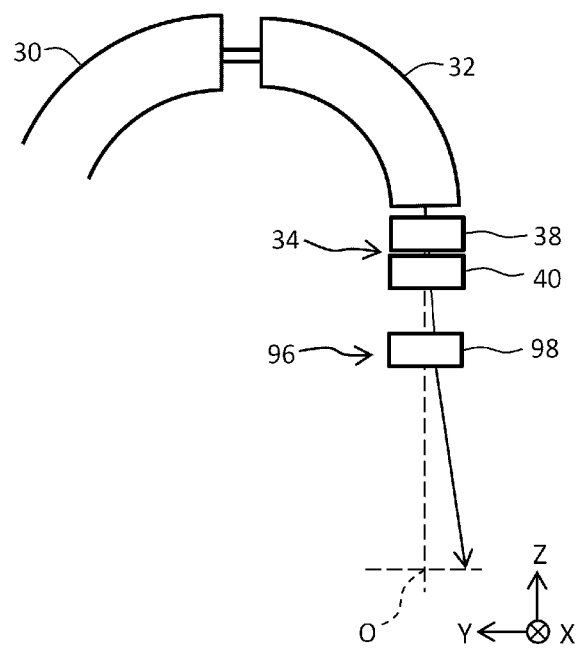
FIG. 10 is a schematic diagram illustrating a third example.

FIG. 10 illuminates an irradiation device according to a third example. In the third example, a scanning unit 96 includes only one shift electromagnet 98. The shift electromagnet 98 performs irradiation field shift toward one direction of the Y direction and the X direction. For example, the shift electromagnet 98 shifts the irradiation field toward the Y direction.

Figure 11:
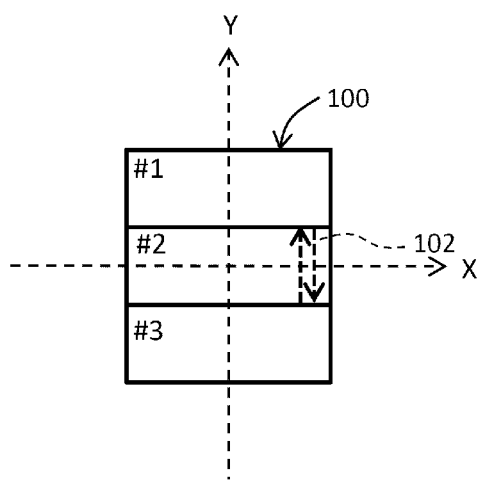
FIG. 11 is a diagram illustrating an expanded irradiation field formed by a third example.

When such a configuration is adopted, an expanded irradiation field 100 illustrated in FIG. 11 can be formed. The expanded irradiation field 100 includes three irradiation field divisions #1 to #3. Each of the irradiation field divisions #1 to #3, that is, each irradiation field, is in a form extending in the X direction in the illustrated example. In the illustrated example, the Y direction is the high-speed scanning direction (see reference numeral 102).

Figure 12:
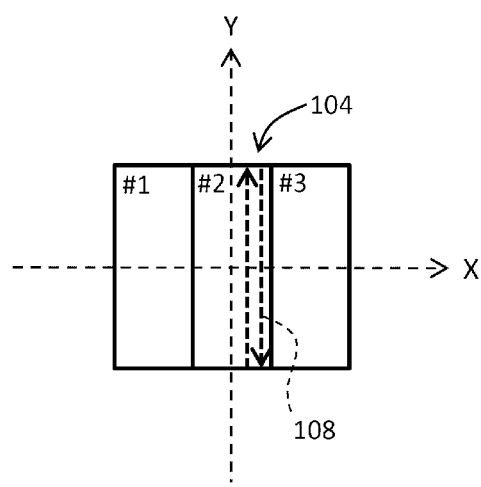
FIG. 12 is a diagram illustrating an expanded irradiation field formed by a fourth example.
Figure 13:
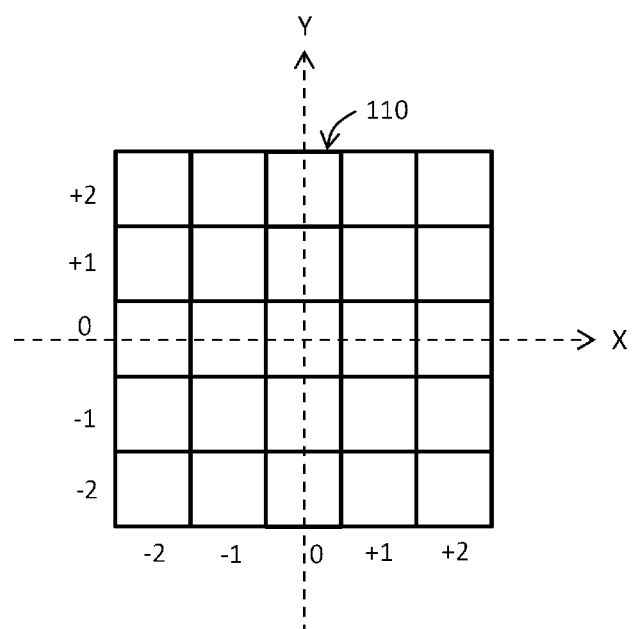
FIG. 13 is a diagram illustrating an expanded irradiation field formed by a fifth example.

FIG. 12 illustrates an expanded irradiation field 104 according to a fourth example. In the fourth example, a configuration basically similar to the configuration illustrated in FIG. 13 is adopted. However, the shift electromagnet 98 shifts the irradiation field toward the X direction. The expanded irradiation field 104 includes three irradiation field divisions #1 to #3. Each of the irradiation field divisions #1 to #3, that is, each irradiation field, is in a form extending in the Y direction in the illustrated example. In the illustrated example, the Y direction is the high-speed scanning direction (see reference numeral 108).

In the third and fourth examples, the order of scanning electromagnets for causing X direction scanning and scanning electromagnets for causing Y direction scanning may be exchanged. Alternatively, the order of scanning electromagnets for causing high-speed scanning and scanning electromagnets for causing low-speed scanning may be exchanged. Forms or sizes of the individual irradiation field divisions may be different from each other.

FIG. 13 illustrates an expanded irradiation field 110 according to a fifth example. In the fifth example, the number (m) of shift stages in the X direction is 5, and the number (n) of shift stages in the Y direction is also 5. Accordingly, the expanded irradiation field 110 including 25 irradiation field divisions is formed. Values of a current are switched to 5 levels (+2, +1, 0, −1, −2) in the X direction, and values of the current are switched to five levels (+2, +1, 0, −1, −2) also in the Y direction. Generally, m is an odd number of 3 or more, and n is also an odd number of 3 or more.

Figure 14:
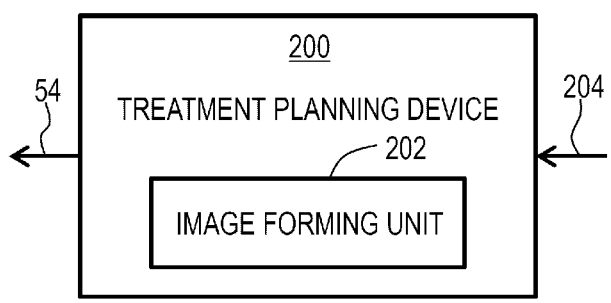
FIG. 14 is a block diagram illustrating a treatment planning device.

FIG. 14 illustrates a treatment planning device 200. The treatment planning device 200 includes, for example, an information processing device. Image information 204 on a living body from an X-ray CT device, an MRI device, or the like is sent to the treatment planning device 200. A treatment plan is made based on the image information 204. The treatment plan information 54 generated by the treatment planning device 200 is sent to the main control unit illustrated in FIG. 1. The treatment planning device 200 includes an image forming unit 202. The image forming unit 202 is a module that forms a reference image by synthesizing division images on a tissue image (cross-sectional image) of a target in the course of making the treatment plan. The image forming unit 202 includes a CPU, an image forming processor, or the like that executes a program.

Figure 15:
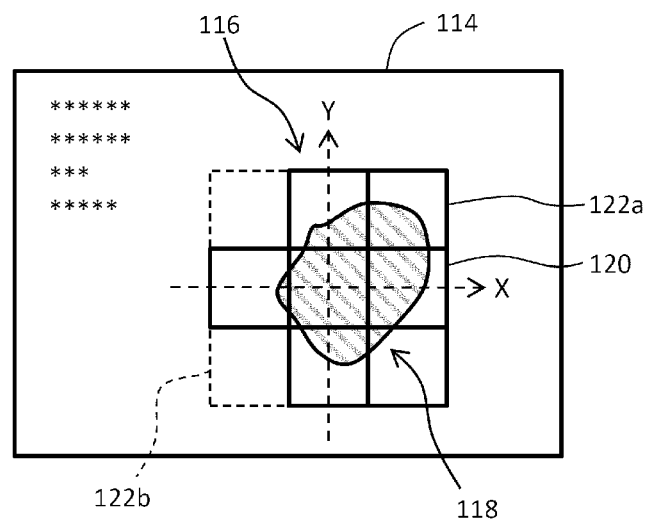
FIG. 15 is a diagram illustrating an example of a reference image displayed in a treatment planning stage.

FIG. 15 illustrates a display image 114 displayed on a display device. The display image 114 includes a reference image 116. The reference image 116 includes a tissue image 118 indicating a tissue of a target or the like, and a division image 120 indicating a plurality of irradiation field divisions. An irradiation field division 122a in which irradiation is performed is represented in a highlighted manner in the division image 120, while an irradiation field division 122b in which irradiation is not performed, that is, not selected by the shift, is represented in a semi-transparent manner. In this manner, whether an irradiation field division is irradiated may be identified and displayed. Reference image 116 may be displayed during treatment.

Figure 16:
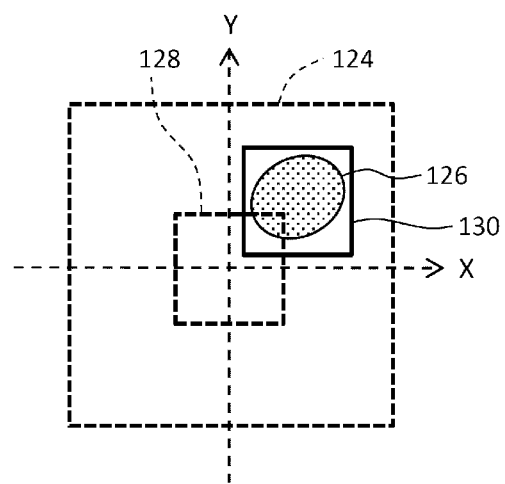
FIG. 16 is a diagram illustrating a first modification.

FIG. 16 illustrates a first modification. Reference numeral 128 indicates an irradiation field in a case where shift is not performed. Reference numeral 124 indicates an expanded irradiation field formed through shift. An irradiation field 130 may be formed within a range of the expanded irradiation field 124 through shift according to a position and size of a target 126. The target 126 is not covered by the irradiation field 128, but is covered by an irradiation field 130 having a same size. According to this configuration, after the irradiation field is set through shift, further shift is not necessary.

Figure 17:
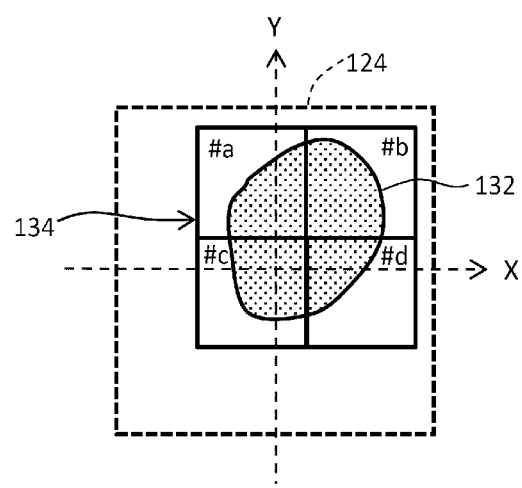
FIG. 17 is a diagram illustrating a second modification.

FIG. 17 illustrates a second modification. In the range of the expanded irradiation field 124, an irradiation field set 134 including four irradiation fields closely connected to each other is set according to a position and size of a target 132. The irradiation field set 134 is an expanded irradiation field in a sense, and includes four irradiation field divisions #1 to #4 as seen from such a viewpoint. According to the second modification, the number of shift can be reduced.

According to the embodiment described above, it is possible to achieve both the miniaturization of the irradiation device and the expansion of the irradiation field by using the scanning unit in which the response characteristic is prioritized and the shift unit in which the deflection characteristic is prioritized. In particular, since the statically controlled shift unit is provided at the post-stage of the dynamically controlled scanning unit, various challenges in designing, manufacturing, and controlling the irradiation device are greatly reduced. The configuration according to the embodiment described above is particularly desirable to be applied to a heavy particle beam therapy device provided with a rotating gantry, and alternatively may be applied to other particle beam therapy devices.

What is claimed is:

1. A particle beam therapy device, comprising:
  a scanning unit that performs scanning with a particle beam to form an irradiation field;
  a shift unit that shifts the irradiation field by deflecting the particle beam emitted from the scanning unit to form an expanded irradiation field; and
  a control unit that dynamically switches operation conditions of the scanning unit in a scanning period in which scanning with the particle beam is performed, and that statically switches operation conditions of the shift unit in an interruption period in which irradiation with the particle beam is not performed.

2. The particle beam therapy device according to claim 1, wherein
  the scanning unit includes:
    a first scanning electromagnet that causes scanning with the particle beam in a first scanning direction orthogonal to a scanning central axial direction; and
    a second scanning electromagnet that causes scanning with the particle beam in a second scanning direction orthogonal to the scanning central axial direction and the first scanning direction, and
  the shift unit includes a first shift electromagnet that shifts the irradiation field in the first scanning direction.

3. The particle beam therapy device according to claim 2, wherein
  a settling time of a magnetic field formed by the first scanning electromagnet is shorter than a settling time of a magnetic field formed by the first shift electromagnet.

4. The particle beam therapy device according to claim 2, wherein
  inductance of the first scanning electromagnet is smaller than inductance of the first shift electromagnet.

5. The particle beam therapy device according to claim 2, wherein
  the number of shift stages in the first scanning direction in the shift unit is m (where m is an odd number of 3 or more).

6. The particle beam therapy device according to claim 2, wherein
  the shift unit includes a second shift electromagnet that shifts the irradiation field in the second scanning direction.

7. The particle beam therapy device according to claim 6, wherein
  the number of shift stages in the first scanning direction in the shift unit is m (where m is an odd number of 3 or more),
  the number of shift stages in the second scanning direction in the shift unit is n (where n is an odd number of 3 or more), and
  the expanded irradiation field is equivalent to a set of m×n irradiation field divisions.

8. The particle beam therapy device according to claim 1, wherein
  whether to shift the irradiation field is determined according to energy of the particle beam.

9. The particle beam therapy device according to claim 1, further comprising:
  a reference image forming unit that forms a reference image including a tissue image, wherein
  the reference image includes a division image that is an image synthesized on the issue image and that represents a plurality of irradiation field divisions formed by shift of the irradiation field, and the reference image is displayed in at least one of a treatment planning stage and a treatment stage.

10. An irradiation field forming method, comprising the steps of:
- forming an irradiation field by performing scanning with a particle beam for treatment; and
- forming an expanded irradiation field by shifting the irradiation field through deflecting the particle beam after the scanning;
- dynamically switching operation conditions of the scanning in a scanning period in which the scanning with the particle beam is performed, and
- statically switching operation conditions of the shifting in an interruption period in which irradiation with the particle beam is not performed.

* * * * *